United States Patent
Callas et al.

(10) Patent No.: US 10,342,600 B2
(45) Date of Patent: *Jul. 9, 2019

(54) SYSTEM AND METHOD FOR INCREASING A TARGET ZONE FOR ELECTRICAL ABLATION

(71) Applicant: AngioDynamics, Inc., Latham, NY (US)

(72) Inventors: Peter Callas, Castro Valley, CA (US); Wesley Chung Joe, Fremont, CA (US)

(*) Notice: Subject to any disclaimer, the term of this patent is extended or adjusted under 35 U.S.C. 154(b) by 255 days.

This patent is subject to a terminal disclaimer.

(21) Appl. No.: 15/140,832

(22) Filed: Apr. 28, 2016

(65) Prior Publication Data
US 2016/0235470 A1 Aug. 18, 2016

Related U.S. Application Data

(63) Continuation of application No. 14/056,315, filed on Oct. 17, 2013, which is a continuation of application No. 13/762,027, filed on Feb. 7, 2013, now Pat. No. 9,414,881.

(60) Provisional application No. 61/596,436, filed on Feb. 8, 2012.

(51) Int. Cl.
*A61B 18/14* (2006.01)
*A61B 18/00* (2006.01)

(52) U.S. Cl.
CPC .... *A61B 18/14* (2013.01); *A61B 2018/00613* (2013.01); *A61B 2018/00827* (2013.01); *A61B 2018/00875* (2013.01); *A61B 2018/143* (2013.01)

(58) Field of Classification Search
CPC .......... A61B 18/14; A61B 2018/00875; A61B 2018/00613; A61B 2018/143
See application file for complete search history.

(56) References Cited

U.S. PATENT DOCUMENTS

| | | | |
|---|---|---|---|
| 2006/0024359 A1* | 2/2006 | Walker et al. | 424/450 |
| 2007/0066957 A1* | 3/2007 | Demarais | A61N 1/0514 604/500 |
| 2010/0030211 A1* | 2/2010 | Davalos et al. | A61B 18/18 606/41 |
| 2010/0250209 A1* | 9/2010 | Pearson et al. | A61B 18/12 703/2 |
| 2012/0059255 A1* | 3/2012 | Paul et al. | A61B 18/14 600/431 |

* cited by examiner

*Primary Examiner* — Eun Hwa Kim
(74) *Attorney, Agent, or Firm* — Peter J. Flora, Esq.

(57) ABSTRACT

System for increasing a target zone for electrical ablation includes a treatment control module executable by a processor. The control module directs a pulse generator to apply pre-conditioning pulses to subject tissue cells in a pre-conditioning zone to electroporation, the pre-conditioning zone being smaller than a target ablation zone. After the pre-conditioning pulses have been applied, the control module directs the pulse generator to apply treatment pulses to electrically ablate the tissue cells in the target ablation zone. The pre-conditioning pulses cause the pre-conditioning zone to have a much higher conductivity so that the zone acts as a larger electrode area when the treatment pulses are applied, which result in a much larger target ablation zone than otherwise possible.

20 Claims, 9 Drawing Sheets

SYSTEM AND METHOD FOR INCREASING A TARGET ZONE FOR ELECTRICAL ABLATION

CROSS REFERENCE TO RELATED APPLICATIONS

This application is a continuation of U.S. application Ser. No. 14/056,315, filed Oct. 17, 2013, which is a continuation of U.S. application Ser. No. 13/762,027, filed Feb. 7, 2013, which claims priority under 35 U.S.C. 119(e) to U.S. Provisional Application No. 61/596,436, filed Feb. 8, 2012, both of which are incorporated by reference herein.

This application is also related to PCT International Application Number PCT/US10129243, filed Mar. 30, 2010 and entitled "System and Method for Estimating a Treatment Region for a Medical Treatment Device and for Interactively Planning a Treatment of a Patient", which is incorporated herein by reference.

FIELD OF THE INVENTION

The present invention relates to a medical treatment device for ablating a target tissue zone. More particularly, the present application relates to a system and method for increasing a target tissue zone for electrical ablation.

BACKGROUND OF THE INVENTION

Devices for delivering therapeutic energy such as an ablation device using irreversible electroporation (IRE) include a pulse generator and one or more electrodes coupled to the generator. The pulse generator delivers the therapeutic energy to a targeted tissue through the electrodes, thereby causing ablation of the tissue.

Once a target treatment area/region is located within a patient, the electrodes of the device are placed in such a way as to create a treatment zone that surrounds the target treatment region.

Prior to treatment, a treatment planning system is used to generate an estimated treatment region that completely covers the target treatment region. The estimated region is used by a physician to plan where to place the electrodes in the patient.

This can be effective when the target area is relatively small, e.g., less than 2 cm in length. However, when the target area is much larger, e.g., larger than 3 cm length, the physician may be forced to use a large number of electrodes, e.g., 4 or more electrodes. This makes accurately placing the electrodes much more difficult as moving one electrode affects the spacing from all other electrodes.

Alternatively, the large target area can be divided into two or more smaller areas and the treatment procedure for one area can be repeated to cover the other divided areas. However, this makes the entire treatment procedure much longer. The longer procedure makes it riskier for the patient since the patient would have to stay on an operating table much longer, often with an exposed body portion to be treated. The longer procedure also makes the procedure more expensive.

Therefore, it would be desirable to provide a system and method for increasing a target tissue zone for electrical ablation for a given set of electrodes.

SUMMARY OF THE DISCLOSURE

Disclosed herein is a system and method of pre-conditioning a target tissue near an electrode to increase a target ablation zone. The system includes a memory, a processor coupled to the memory and a treatment control module. The treatment control module stored in the memory and executable by the processor, the treatment control module applies through at least one electrode a plurality of pre-conditioning pulses to subject tissue cells in a pre-conditioning zone surrounding the electrode to electroporation, the pre-conditioning zone being smaller than a target ablation zone. After the ore-conditioning pulses have been applied, the control module applies a plurality of treatment pulses in an amount sufficient to electrically ablate the tissue cells in the target ablation zone. Advantageously, the pre-conditioning pulses cause the pre-conditioning zone to have a much higher conductivity so that the zone acts as a larger electrode area when the treatment pulses are applied, which results in a much larger target ablation zone than otherwise possible.

In another aspect, the treatment control module applies the plurality of treatment pulses in an amount sufficient to subject the tissue cells in the target ablation zone to irreversible electroporation or supra-poration.

In another aspect, the treatment control module applies the pre-conditioning pulses that have a shorter pulse width than the treatment pulses.

In another aspect, the treatment control module applies the pre-conditioning pulses in an amount sufficient to subject tissue cells in the pre-conditioning zone to irreversible electroporation.

In another aspect, the treatment control module waits at least 30 seconds after the pre-conditioning pulses have been applied to allow an electrical conductivity in the pre-conditioning zone to increase.

In another aspect, the treatment control module waits at least two minutes after the pre-conditioning pulses have been applied to allow an electrical conductivity in the pre-conditioning zone to increase.

In another aspect, while the pre-conditioning pulses are being applied, the treatment control module continuously monitors current to adjust at least one pulse parameter for the pre-conditioning pulses.

In another aspect, after the pre-conditioning pulses have been applied, the treatment control module continuously monitors impedance and determines when to apply the treatment pulses.

In another aspect, the treatment control module applies the pre-conditioning pulses that have a shorter pulse width than the treatment pulses, and waits at least 30 seconds after the pre-conditioning pulses have been applied to allow an electrical conductivity in the pre-conditioning one to increase.

In another aspect, the treatment control module applies a test pulse through the electrode and determines at least one pulse parameter for the pre-conditioning pulses based on the applied test pulse.

In another aspect, treatment control module applies a test pulse through the electrode after the pre-conditioning pulses have been applied, and based on the applied test pulse, determines whether to repeat the application of the pre-conditioning pulses or proceed to application of the treatment pulses.

In another aspect, the treatment control module determines whether to repeat the application of the pre-conditioning pulses based on an electrical conductivity derived from the test pulse.

According to another aspect of the invention, a method for increasing a target zone for electrical ablation is provided. The method includes positioning at least one electrode near a target ablation zone and applying through the positioned electrode a plurality of pre-conditioning pulses to subject tissue cells in a pre-conditioning zone surrounding the electrode to electroporation, the pre-conditioning zone being smaller than the target ablation zone. After the pre-conditioning pulses have been applied, the method further includes applying a plurality of treatment pulses in an amount sufficient to electrically ablate the tissue cells in the target ablation zone.

DETAILED DESCRIPTION OF THE INVENTION

Throughout the present teachings, any and all of the one, two, or more features and/or components disclosed or suggested herein, explicitly or implicitly, may be practiced and/or implemented in any combinations of two, three, or more thereof, whenever and wherever appropriate as understood by one of ordinary skill in the art. The various features and/or components disclosed herein are all illustrative for the underlying concepts, and thus are non-limiting to their actual descriptions. Any means for achieving substantially the same functions are considered as foreseeable alternatives and equivalents, and are thus fully described in writing and fully enabled. The various examples, illustrations, and embodiments described herein are by no means, in any degree or extent, limiting the broadest scopes of the claimed inventions presented herein or in any future applications claiming priority to the instant application.

Figure 1:
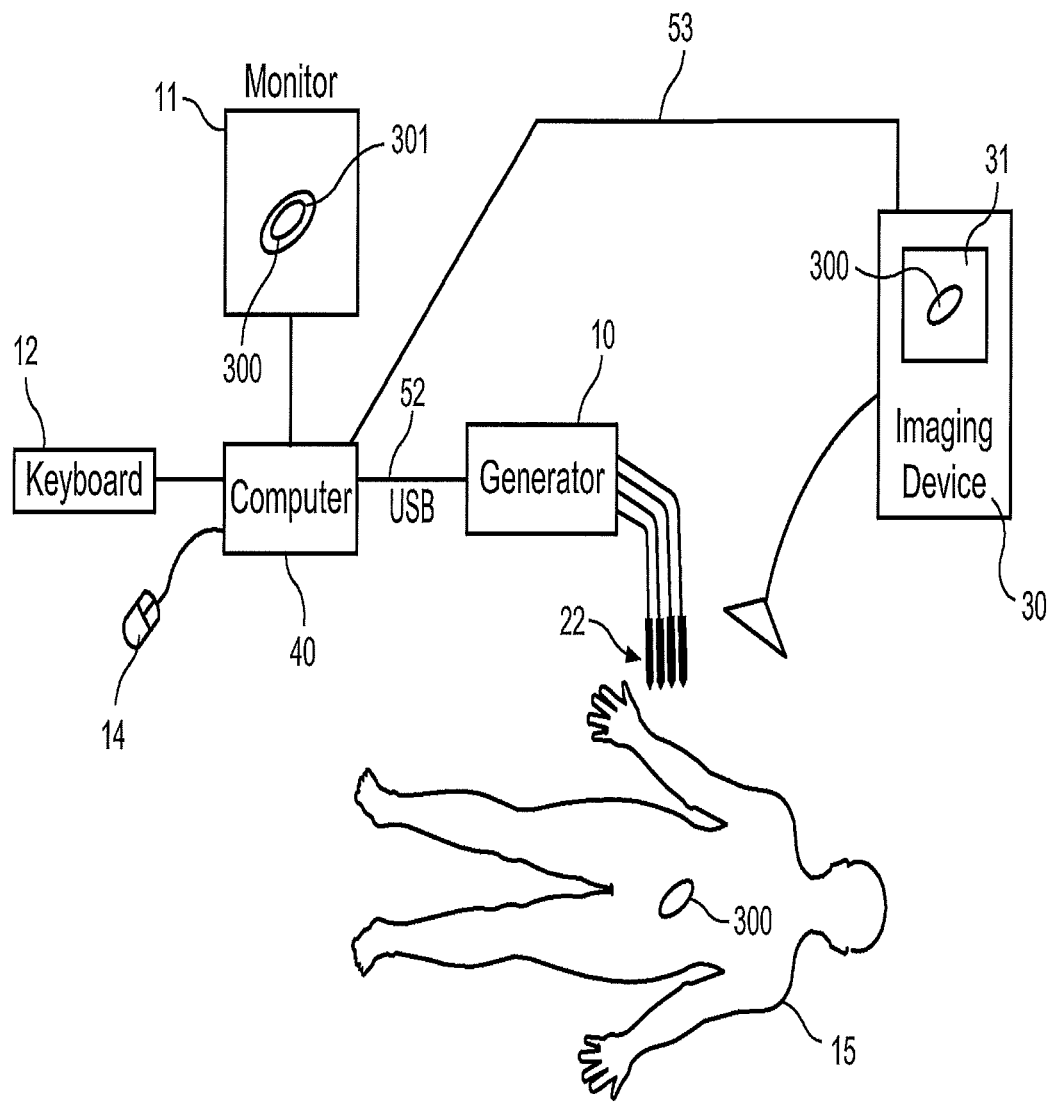
FIG. 1 illustrates several components of a medical treatment system to treat a patient according to the present invention.

One embodiment of the present invention is illustrated in FIG. 1. One or more probes/electrodes 22 deliver therapeutic energy and are powered by a voltage pulse generator 10 that generates high voltage pulses as therapeutic energy such as pulses capable of irreversibly electroporating the tissue cells. In the embodiment shown, the voltage pulse generator 10 includes six separate receptacles for receiving up to six individual probes 22 which are adapted to be plugged into the respective receptacle. The receptacles are each labeled with a number in consecutive order. In other embodiments, the voltage pulse generator can have any number of receptacles for receiving more or less than six probes.

In the embodiment shown, each probe 22 includes either a monopolar electrode or bipolar electrodes having two electrodes separated by an insulating sleeve. In one embodiment, if the probe includes a monopolar electrode, the amount of exposure of the active portion of the electrode can be adjusted by retracting or advancing an insulating sleeve relative to the electrode. See, for example, U.S. Pat. No. 7,344,533, which is incorporated by reference herein. The generator 10 is connected to a treatment control computer 40 having input devices such as keyboard 12 and a pointing device 14, and an output device such as a display device 11 for viewing an image of a target treatment region such as a lesion 300 surrounded by a safety margin 301. The pulse generator 10 is used to treat a lesion 300 inside a patient 15. An imaging device 30 includes a monitor 31 for viewing the lesion 300 inside the patient 15 in real time. Examples of imaging devices 30 include ultrasonic, CT, MRI and fluoroscopic devices as are known in the art.

The present invention includes computer software (treatment control module 54) which assists a user to plan for, execute, and review the results of a medical treatment procedure, as will be discussed in more detail below. For example, the treatment control module 54 assists a user to plan for a medical treatment procedure by enabling a user to more accurately position each of the probes 22 of the pulse generator 10 in relation to the lesion 300 in a way that will generate the most effective treatment zone. The treatment control module 54 can display the anticipated treatment zone based on the position of the probes and the treatment parameters. The treatment control module 54 can display the progress of the treatment in real time and can display the results of the treatment procedure after it is completed. This information can be used to determine whether the treatment was successful and whether it is necessary to re-treat the patient.

For purposes of this application, the terms "Code", "software", "program", "application", "software code", "software module", "module" and "software program" are used interchangeably to mean software instructions that are executable by a processor.

The "user" can be a physician or other medical professional. The treatment control module 54 executed by a processor outputs various data including text and graphical data to the monitor 11 associated with the generator 10.

Figure 2:
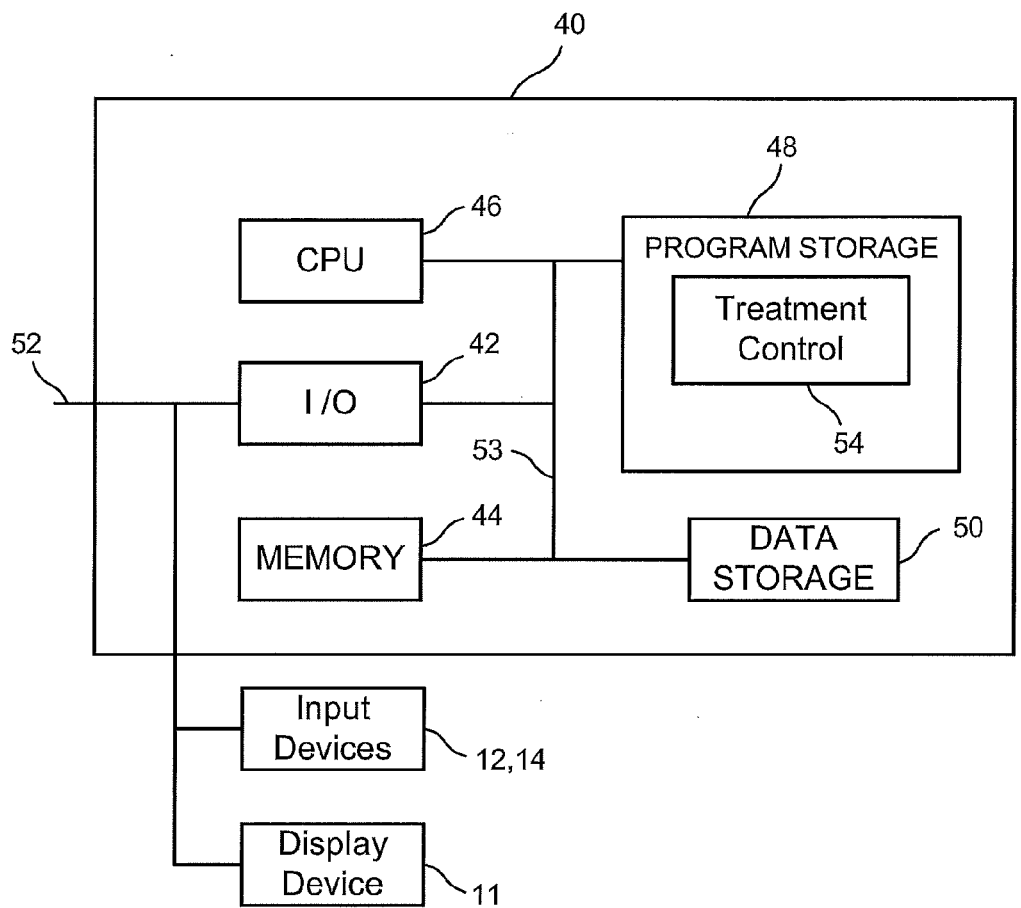
FIG. 2 is a schematic diagram of a treatment control computer of the present invention.

Referring now to FIG. 2, the treatment control computer 40 of the present invention manages planning of treatment for a patient. The computer 40 is connected to the communication link 52 through an I/O interface 42 such as a USB (universal serial bus) interface, which receives information from and sends information over the communication link 52 to the voltage generator 10. The computer 40 includes memory storage 44 such as RAM, processor (CPU) 46, program storage 48 such as ROM or EEPROM, and data storage 50 such as a hard disk, all commonly connected to each other through a bus 53. The program storage 48 stores, among others, a treatment control module 54 which includes a user interface module that interacts with the user in planning for, executing and reviewing the result of a treatment Any of the software program modules in the program storage 48 and data from the data storage 50 can be transferred to the memory 44 as needed and is executed by the CPU 46.

In one embodiment, the computer 40 is built into the voltage generator 10. In another embodiment, the computer 40 is a separate unit which is connected to the voltage generator through the communication link 52. In a preferred embodiment, the communication link 52 is a USB link.

In one embodiment, the imaging device 30 is a stand alone device which is not connected to the computer 40. In the embodiment as shown in FIG. 1, the computer 40 is connected to the imaging device 30 through a communication link 53. As shown, the communication link 53 is a USB link. In this embodiment, the computer can determine the size and orientation of the lesion 300 by analyzing the data such as the image data received from the imaging device 30, and the computer 40 can display this information on the monitor 11. In this embodiment, the lesion image generated by the imaging device 30 can be directly displayed on the grid 200 of the monitor 11 of the computer running the treatment control module 54. This embodiment would provide an accurate representation of the lesion image on the grid 200, and may eliminate the step of manually inputting the dimensions of the lesion in order to create the lesion image on the grid 200. This embodiment would also be useful to provide an accurate representation of the lesion image if the lesion has an irregular shape.

The basic functionality of the computer software (treatment control module 54) will now be discussed in relation to the following example.

It should be noted that the software can be used independently of the generator 10. For example, the user can plan the treatment in a different computer as will be explained below and then save the treatment parameters to an external memory device, such as a USB flash drive (not shown). The data from the memory device relating to the treatment parameters can then be downloaded into the computer 40 to be used with the generator 10 for treatment.

Figure 3:
FIG. 3 is a screen shot of an "Information" screen of a treatment control module showing various input boxes.

After the treatment control module 54 is initialized, it displays an "Information" screen with various input boxes as shown in FIG. 3. A keyboard or other input device 12, together with a mouse or other pointing device 14 (see FIG. 1) are used to input the data. Any data that is inputted into the input boxes can be saved into internal or external memory along with a record of the treatment as described below for future reference. The basic patient information can be inputted, such as a patient ID number in input box 100, the name of the patient in input box 101, and the age of the patient in input box 102. The user can enter clinical data, such as the clinical indication of the treatment in input box 114. The date of the procedure is automatically displayed at 111 or can be inputted by the user in another embodiment. The user can enter other case information such as the name of the physician in input box 112 and any specific case notes in input box 113.

The dimensions of the lesion 300 are determined from viewing it on the monitor 31 of the imaging device 30 (see FIG. 1) such as an ultrasonic imaging device and using known methods to calculate the dimensions from the image generated from the imaging device 31. The dimensions of the lesion 300 (length at input box 103, width at input box 104, and depth at input box 105) are inputted into the program. A safety margin is selected at input box 106 which will surround the entire lesion 300 in three dimensions. According to the size of the safety margin that is selected, a target treatment region is automatically calculated and is displayed in boxes 107, 108, and 109 as shown. In one embodiment, the safety margin value may be set to zero. For example, when treating a benign tumor, a safety margin may not be necessary.

In the embodiment shown in FIG. 3, the user has indicated that the lesion that will be treated has a length of 2 cm, width of 1 cm and a depth of 1 cm. With a user specified margin, of 1 cm (which is a default margin setting), the target treatment region has a length of 4 cm, width of 3 cm and a depth of 3 cm.

The user can select the "ECG synchronization" option by clicking the circle in the box 110 in order to synchronize the pulses with an electrocardiogram (ECG) device, if such a device is being used during the procedure. The other options available for treatment that are Included in box 110 can include an option for "90 PPM" (pulses per minute) or "240 PPM". The user should select at least one of the three options provided in box 110. After all of the necessary data has been inputted, the user clicks on the "Next" button with a pointing device 14 to proceed to the next screen described below.

Further regarding the ECG synchronization option, if this circle is selected in window 110, the treatment control module 54 will test this functionality to verify that the system is working properly. The treatment control module 54 can automatically detect whether an error leas occurred during the testing phase of the EGG feature. The detectable errors include, but are not limited to, "no signal" (such as no pulses for 3.5 seconds) and "noisy" (such as pulses occurring at a rate greater an 120 beats per minute for at least 3.5 seconds).

The treatment control module 54 can synchronize energy release with cardiac rhythm by analyzing cardiac output such as electrocardiogram results (or other cardiac function output) and sending synchronization signals to a controller of the pulse generator 10. The control module 54 is also capable of generating internal flags such as a synchronization problem flag and a synchronization condition flag to indicate to users on a graphic user interface a synchronization status, so that energy pulse delivery can be synchronized with the cardiac rhythm for each beat (in real-time) or aborted as necessary for patient safety and treatment efficiency.

Specifically, the control module 54 synchronizes energy pulses such as IRE (irreversible electroporation) pulses with a specific portion of the cardiac rhythm. The module uses the R-wave of the heartbeat and generates a control signal to the pulse generator 10 indicating that this portion of the heartbeat is optimal for release of IRE pulses. For clarity, the S wave would be an optimal time for delivery of an energy pulse, but due to the fact that the S wave ends nebulously in some cases, the R wave is used as an indicator to start timing of energy release.

More specifically, the synchronization feature of the control module 54 allows for monitoring of heart signals so as to ensure that changes, maladies, and other alterations associated with the heartbeat are coordinated such that pulses from the pulse generator 10 are released at the proper time, and that if the heartbeat is out of its normal rhythm, that the release of energy is either altered or aborted.

Next, the user can select the number of probes that the user believes will be necessary to produce a treatment zone which will adequately cover the lesion 300 and any safety margin 301. The selection is made by clicking the circle flex each type of device, as shown in the "Probe Selection" screen, illustrated in FIG. 4.

In one embodiment, a "Probes Selection Status" box 199 identifies of the receptacles, if any, on the generator 10 have been connected to a probe by displaying the phrase "Connected" or the like next to the corresponding probe number. In one embodiment, each receptacle includes an RFID device and a connector for each probe which connects to the receptacle and includes a compatible RFID device, so that the treatment control module 54 can detect whether or not an authorized probe has been connected to the receptacle on the generator 10 by detecting a connection of the compatible RFID devices. If an authorized probe is not connected to a receptacle on the generator, the phrase "Not Connected" or the like will appear next to the probe number. In addition, the color of each probe shown in the "Probes Selection Status" box 199 can be used to indicate whether or, not each receptacle on the generator is connected to a compatible probe. This feature allows the user to very that the requisite number of probes are properly connected to the generator 10 before selecting a probe type for the treatment procedure. For example, if the treatment control module 54 detects a problem with the probe connection status (e.g. selecting a three probe array when only two probes are connected to the generator) it can notify the user by displaying an error message.

The user can select which of the connected probes will be used to perform the treatment procedure, by clicking on the box next to the selected probes in the "Probes Selection Status" box 199. By default the treatment control module 54 will automatically select probes in ascending numerical order, as they are labeled.

Figure 4:
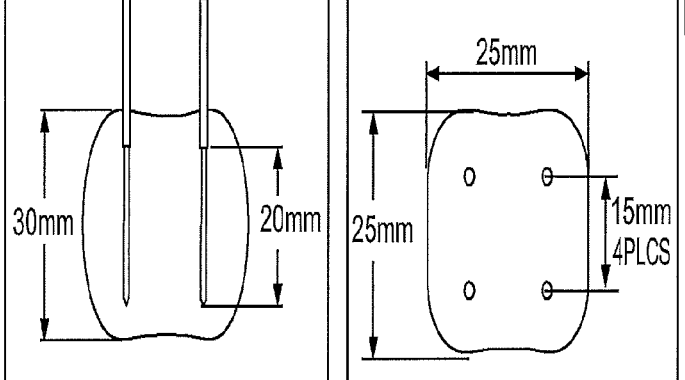
FIG. 4 is a screen shot of a "Probe Selection" screen of the treatment control module showing a side view and top view of the four probe array and an example of the general shape of the treatment zone that can be generated by a four probe array.

Referring to FIG. 4, circle 150 is used to select a four probe array. FIG. 4 illustrates a side view 151 and top view 152 of the four probe array and an example of the general shape of the treatment zone that can be generated by a four probe array. In the illustrated example, the exposed portion of each of the electrodes as shown is 20 mm in length and each pair of the four probes are equally spaced from each other by 15 mm, as measured at four places (PLCS) along the perimeter.

Figure 5:
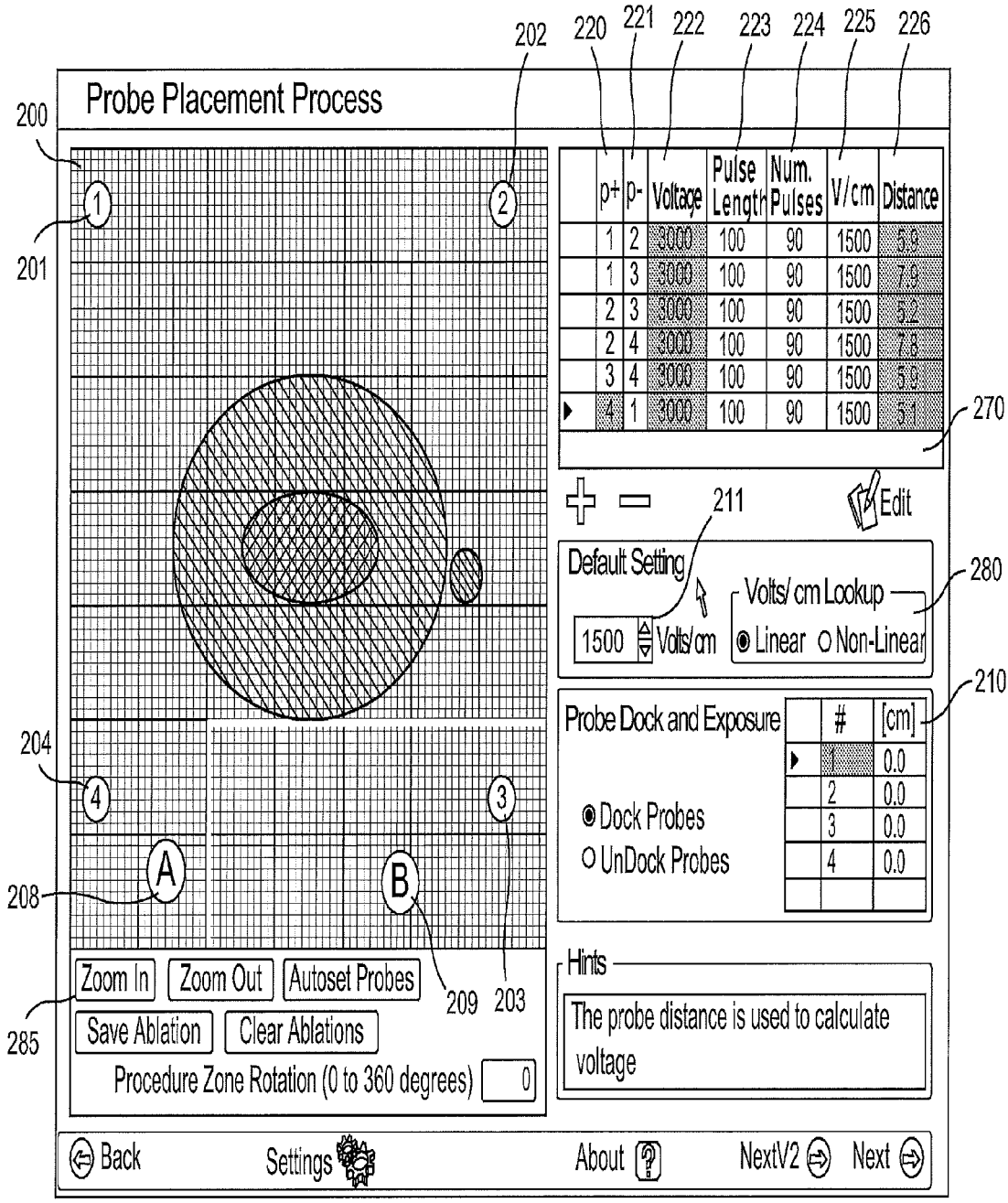
FIG. 5 is a screen shot of a "Probe Placement Process" screen of the treatment control module.

FIG. 5 illustrates a "Probe Placement Process" screen of one aspect of the invention. The screen illustrated by FIG. 5 shows a lesion 300 according to the dimensions which were inputted on the "Information" screen (see FIG. 3) along with a safety margin 301, if any, that was previously inputted. In the example depicted in FIG. 5, the lesion 300 has a length of 2.0 cm and a width of 1.0 cm, and the device selected on the "Probe Selection" screen (see FIG. 4) is a four probe array. The lesion 300 is displayed near the center of an x-y grid 200 with the distance between two adjacent grid lines representing 1 mm. Each of the four probes 201, 202, 203, 204 is displayed in the grid 200 and each probe can be manually positioned within the grid by clicking and dragging the probe with the pointing device 14. Two fiducials 208, 209 labeled "A" and "B", respectively, are also, displayed on the grid 200 and are used as a point of reference or a measure as will be described below.

The amount of longitudinal exposure of the active electrode portion for each probe that has already been manually adjusted by the user as explained above can be manually inputted in input box 210, which can be selected by the user according to the depth (z) of the lesion. In this way, the treatment control module 54 can generate an estimated treatment zone according to the treatment parameters, and locations and depths of the probes. In one embodiment, a second x-z grid is displayed on the monitor 11 of the computer running the treatment control module 54. In one embodiment, the treatment control module 54 can automatically calculate preferred values for the amount of longitudinal exposure of the active electrode portions based on the size and shape of the lesion. The depth (z) of the electric field image can be calculated analytically or with interpolation and displayed on the x-z grid. Because the distribution of the electric field (i.e., expected treatment region) between two monopolar electrodes may "dip in" along the boundary line (e.g., a peanut shaped treatment region due to large spacing between the two electrodes where the width of the region is smaller in the middle; see for example region 305 in FIG. 9) depending on the electrode location and the applied voltage, it is beneficial to have an x-z grid included on the monitor. For example, if this "dip" of the boundary line travels into, rather than surround/cover, the lesion region, then the targeted region may not be fully treated. As a default to ensure treatment of the entire lesion region, the probe depth placement and the exposure length may be set unnecessarily higher to ensure erring on the safe side. However, this will potentially treat an much larger volume than needed, killing healthy surrounding tissue, which can be an issue when treating sensitive tissues such as the pancreas, brain, etc. By optimizing the treatment depth (z) together with the width (x) and height (y), this effect may be reduced, further enhancing procedural protocol and clinical outcome.

The probe dock status is indicated in box 210, by indicating if the probes are "docked" or "undocked". The "UnDock Probes" button allows the user to "unplug" the probes from the generator while the "Probe Placement Process" screen is displayed without causing error messages. In normal operation, the user plugs the probes into the generator on the "Probe Selection" screen, and then the probes are "authorized" as being compatible probes according to the RFID devices, as discussed above. When the user proceeds to the "Probe Placement Process" screen, the software requires that all the selected probes remain plugged into the generator, or else the software will display an error message (e.g. "Probe #2 unplugged", etc.), and will also force the user back to the "Probe Selection" screen. However, sometimes doctors may want to perform another scan of the lesion or perform some other procedure while leaving the probes inserted in the patient. But, if the procedure cannot be performed near the generator, the probes are unplugged from the generator. If the user selects the "UnDock Probes" button, this will allow the probes to be unplugged from the generator without causing an error message. Then, after the user has performed the other procedure that was required, he can re-attach the probes to the generator, and then select "Dock Probes" in input box 210. In this way, the user will not receive any error messages while the "Probe Placement Process" screen is displayed.

There is a default electric field density setting (Volts/cm) which is shown in input box 211. In the example, the default setting is 1500 Volts/cm. This number represents the electric field density that the user believes is needed to effectively treat the cells, e.g., ablate the tissue cells. For example, 1500 Volts/cm is an electric field density that is needed to irreversibly electroporate the tissue cells. Based on the number selected in input box 211, the treatment control module 54 automatically adjusts the voltage (treatment energy level) applied between the electrodes, as shown in column 222.

Box 280 allows a user to select between two different Volts/cm types, namely "Linear" or "Non-Linear Lockup".

The default Volts/cm setting is "Linear", in which case the Voltage that is applied between a given pair of electrodes, as shown in column 222, is determined by the following formula:

$$\text{Voltage} = xd, \quad (1)$$

where x=the electric field density setting (Volts/cm) shown in column 225, which is based on the value from box 211, and where d=the distance (cm) between the given pair of electrodes shown in column 228.

Therefore, when "Linear" is selected, the Voltage that is applied between a given pair of electrodes is directly proportional to the Distance between the given electrode pair in a linear relationship.

If the user selects "Non-Linear Lookup" in box 280, then the Voltage that is applied between the given pair of electrodes will be similar to the Voltage values for a "Linear" selection when a pair of electrodes are closely spaced together (e.g. within about 1 cm). However, as a pair of given electrodes are spaced farther from one another, a "Non-Linear Lookup" will produce lower Voltages between the given pair of electrodes as compared to the Voltage values for a "Linear" selection at any given distance. The "Non-Linear Lookup" feature is particularly useful for reducing "popping" during treatment. "Popping" refers to an audible popping noise that sometimes occurs, which is believed to be caused by a plasma discharge from high voltage gradients at the tip of the electrodes. The "Non-Linear Lookup" feature can also minimize any swelling of the tissue that might occur as a result of a treatment. The Voltage values used for the "Non-Linear Lookup" selection can be pre-determined based on animal experiments and other research. In one embodiment, different tissue types can each have their own "Non-Linear Lookup" table. In the example shown, the tissue being treated is prostate tissue.

The details of the treatment parameters are displayed in window 270. The firing (switching) sequence between probes is listed automatically in window 270. In the example, the firing sequence involves six steps beginning with between probes 1 and 2, then probes 1 and 3, then probes 2 and 3, then probes 2 and 4, then probes 3 and 4, and then probes 4 and 1. As shown, the polarity of each of the probes may switch from negative to positive according to step of the firing sequence. Column 220 displays which probe is the positive probe (according to a number assigned to each probe) for each step. Column 221 displays which probe is the negative probe (according to a number assigned to each probe) for each step. Column 222 displays the actual voltage generated between each probe during each step of the firing sequence. In the example, the maximum voltage that can be generated between probes is limited by the capabilities of the generator 10, which in the example is limited to a maximum of 3000 Volts. Column 223 displays the length of each pulse that is generated between probes during each respective step of the firing sequence. In the example, the pulse length is predetermined and is the same for each respective step, and is set at 100 microseconds. Column 224 displays the number of pulses that is generated during each respective step of the firing sequence. In the example, the number of pulses is predetermined and is the same for each respective step, and is set at 90 pulses which are applied in a set of 10 pulses at a time. Column 225 displays the setting for Volts/cm according to the value selected at input box 211. Column 226 displays the actual distance between the electrodes (measured in cm), which is automatically calculated according to the placement of each probe in the grid 200.

The treatment control module 54 can be programmed to calculate and display the area of the combined treatment regions on the grid 200 by several different methods.

Figure 6:
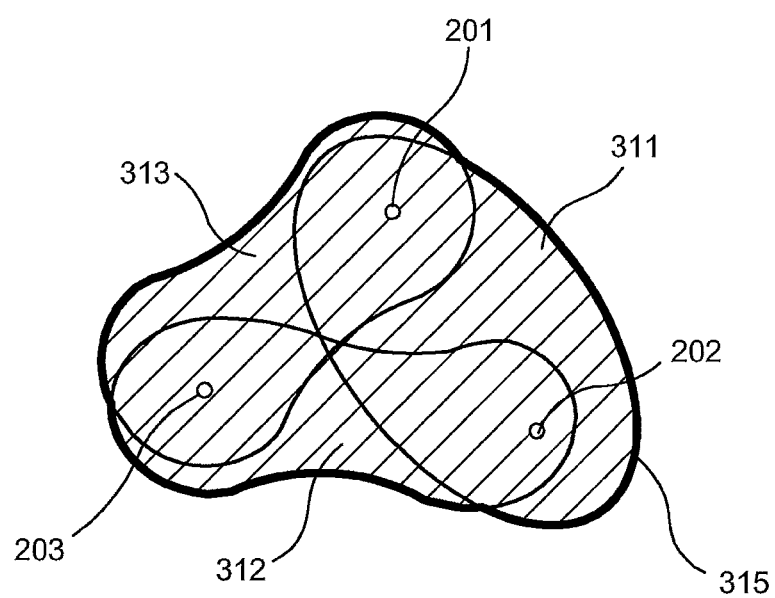
FIG. 6 illustrates an example of a three probe array defining three individual treatment zones, which combine to form a combined treatment region.

Each method determines a boundary line surrounding a treatment zone that is created between a pair of electrodes. By combining a plurality of treatment zones with each treatment zone being defined by a pair of electrodes, a combined treatment region can be displayed on the x-y grid. FIG. 6 illustrates three electrodes 201 (E1), 202 (E2), 203 (E3) defining three individual treatment zones 311, 312, 313, which combine to form a combined treatment region 315 which is shown with hatched lines.

As discussed above, the monitor can further include an x-z grid to illustrate the depth of the lesion and the shape of the treatment region. The shape of the treatment zone in the x-z grid will vary according to the selected amounts of electrode exposure for each probe and can be determined by one or more methods.

In one embodiment, the treatment boundary line that is created between two points on the x-y grid can be rotated about an axis joining the two points in order to generate the treatment region boundary line on the x-z grid. In this embodiment, several points may be selected along the exposed length of the active electrode portion for each probe at various depths (z). A three-dimensional combined treatment region can then be generated by determining the boundary line on the x-y grid between each individual pair of points and then rotating the boundary line along the axis joining each pair of points. The resulting boundary lines can be combined to create a three dimensional image that is displayed on the monitor.

The following is an alternate method for determining a boundary line on the x-z grid, thereby determining a three dimensional treatment region. This example describes a two probe array with the probes being inserted in a parallel relationship and with the probes having the same amount of exposed portions of the electrode. In this example, the exposed portions of each probe start at the same "uppermost" depth (z) and end at the same "lowermost" depth (z). First, a treatment zone boundary line is created in the x-y plane at the uppermost depth (z). Next, the treatment zone boundary line is repeatedly created stepwise for all subsequently lower depths (z), preferably evenly spaced, until the lowermost depth (z) is reached. The result is a 3-D volume (stacked set of treatment zone boundary lines) having a flat top surface and a flat bottom surface. Next, two new focus points are selected, with the first focus point positioned midway between the probe positions in the x-y grid and near the uppermost depth (z) of the exposed electrode. The second focus point is also positioned midway between the probe positions in the x-y grid, but near the lowermost depth (z) of the exposed electrode. Next, a treatment zone boundary line is created in the x-z grid using one of the methods described earlier. The actual placement of each focus point may be closer together, namely, not positioned in the uppermost and lowermost x-y planes defined by the exposed portions. The placement of each focus point should be selected so that the treatment zone boundary line that is created in the x-z grid closely matches the treatment zone boundary lines that were created in the uppermost and lowermost x-y grids. Next, the treatment zone boundary line that was created in the x-z grid according to the two focus points is rotated about the axis joining the two focus points. This creates the shapes for the upper and lower 3-D volumes which are added to the flat top surface and the flat bottom surface described above.

The above methods can be applied by persons of ordinary skill in the art to create 3-D treatment zones between exposed portions of electrodes even when the probes are not parallel to each other and even when e amount of the exposed portion varies with each probe.

Furthermore, there are situations where it is advantageous to show multiple boundary zones as a result of a therapy. For example, indicating which regimes undergo no change, reversible electroporation, Irreversible electroporation, and conventional thermal damage possible in accordance with the present invention. In addition, it is possible to output the entire distribution rather than just delineating boundaries.

It has been shown repeatedly in the literature that tissue properties are highly variable between tissue types, between individuals, and even within an individual. These changes may result from differences in body fat composition, hydration levels, and hormone cycles. Due to the large dependence of IRE (irreversible electroporation) treatments on tissue conductivity, it is imperative to have accurate values. Therefore, to obtain viable conductivity values prior to treatment, a low amplitude voltage pulse is used between the electrode conductors and the resultant impedance/conductance is measured as a way to determine pertinent tissue property data such as the predicted current. The value determined may then be implemented when assessing field strength and treatment protocol in real time. For example, the resulting impedance or predicted current can be used to set the default electric field density.

One method of generating an estimated treatment region between a pair of treatment electrodes is a numerical model based method involving finite element analysis (PEA). For example, U.S. Patent Application Publication No. 2007/0043345, which is hereby incorporated by reference, discloses using FEA models to generate treatment zones between a pair of electrodes (the calculations were performed using MATLAB's finite element solver, Fernlab v2.2 (The MathWorks, Inc. Natick, Mass.)).

Most engineering problems can be solved by breaking the system into cells where each corner of the cell or mesh is a node. FEA is used to relate each node to each of the other nodes by applying sets of partial differential equations. This type of a system can be coded by scratch, but most people use one of many commercial FEA programs that, automatically define the mesh and create the equations given the model geometry and boundary conditions. Some PEA programs only work in one area of engineering, for example, heat transfer and others are known as multiphysics. These systems can convert electricity to heat and can be used for studying the relationships between different types of energy.

Typically the FEA mesh is not homogeneous and areas of transition have increased mesh density. The time and resources (memory) required to solve the FEA problem are proportional to the number of nodes, so it is generally unwise to have a uniformly small mesh over the entire model. If possible, FEA users also try to limit the analysis to 20 problems and/or use planes of symmetry to limit the size of the model being considered because even a modest 2D model often requires 30 minutes to several hours to run. By comparison, a 3D Model usually takes several hours to several days to run. A complicated model like a weather system or a crash simulation may take a super computer several days to complete.

Depending on the complexity of the FEA models that are required, the purchase price of the FEA modeling software can cost several thousand dollars for a low end system to $30 k for a non linear multiphysics system. The systems that model the weather are custom made and cost tens of millions of dollars.

In one example, the steps which are required for generating a treatment zone between a pair of treatment probes using finite element analysis include: (1) creating the geometry of interest (e.g., a plane of tissue with two circular electrodes); (2) defining the materials involved (e.g., tissue, metal); (3) defining the boundary conditions (e.g., Initial voltage, Initial temperature); (4) defining the system load (e.g., change the voltage of the electrodes to 3,000V); (5) determining the type of solver that will be used; (6) determining whether to use a time response or steady state solution; (7) running the model and wait for the analysis to finish; and (8) displaying the results.

Using FEA, however, may not be practical for use in calculating and displaying in real time a treatment zone that is created between a pair of treatment probes in accordance with the present invention because of the time required to run these types of analyses. For the present invention, the system should allow a user to experiment with probe placement and should calculate a new treatment zone in less than a few seconds. Accordingly, the FEA model is not appropriate for such use and it would be desirable to find an analytic solution (closed form solution), which can calculate the treatment zones with only simple equations, but which closely approximate the solutions from a numerical model analysis such as the finite element analysis. The closed loop solutions should preferably generate the treatment zone calculation in a fraction of a second so as to allow a physician/user to experiment with probe placement in real time.

There are different closed loop (analytical model analysis) methods for estimating and displaying a treatment zone between a pair of treatment probes, which produce similar results to what would have been derived by a numerical model analysis such as FEA, but without the expense and time of performing FEA. Analytical models are mathematical models that have a closed form solution, i.e., the solution to the equations used to describe changes in a system can be expressed as a mathematical analytic function. The following method represents just one of the non-limiting examples of such alternative closed loop solutions.

In mathematics, a Cassini oval is a set (or locus) of points in the plane such that each point p on the oval bears a special relation to two other fixed points $q_1$ and $q_2$; the product of the distance from p to $q_1$ and the distance from p to $q_2$ is constant. That is, if the function dist(x,y) is defined to be the distance from a point x to a point y, then all points p on a Cassini oval satisfy the equation:

$$\text{dist}(q_1,p) \times \text{dist}(q_2,p) = b^2 \qquad (2)$$

where b is a constant.

The points $q_1$ and $q_2$ are called the foci of the oval.

Suppose $q_1$ is the point (a,0), and $q_2$ is the point (−a,0). Then the points on the curve satisfy the equation:

$$((x-a)^2+y^2)((x+a)^2+y^2) = b^4 \qquad (3)$$

The equivalent polar equation is:

$$r^4 - 2a^2 r^2 \cos 2\theta = b^4 - a^4 \qquad (4)$$

The shape of the oval depends on the ratio b/a. When b/a is greater than 1, the locus is a single, connected loop. When b/a is less than 1, the locus comprises two disconnected loops. When b/a is equal to 1, the locus is a lemniscate of Bernoulli.

The Cassini equation provides a very efficient algorithm for plotting the boundary line of the treatment zone that was created between two probes on the grid 200. By taking pairs of probes for each firing sequence, the first probe is set as $q_1$ being the point (a,0) and the second probe is set as $q_2$ being the point (−a,0).

The polar equation for the Cassini curve is preferably used because it provides a more efficient equation for computation. The current algorithm can work equally as well by using the Cartesian equation of the Cassini curve. By solving for $r^2$ from eq. (4) above, the following polar equation was developed:

$$r^2 = a^2 \cos(2*\text{theta}) +/- \text{sqrt}(b^4 - a^4 \sin^2(2*\text{theta})) \qquad (5)$$

where a=the distance from the origin (0,0) to each probe in cm; and where b is calculated from the following equation:

$$b^2 = \left[\frac{V}{[\ln(a)(595.28) + 2339]\left(\frac{A}{650}\right)}\right]^2 \quad (6)$$

where V=the Voltage (V) applied between the probes;
where a=the same a from eq. (5); and
where A=the electric field density (V/cm) that is required to ablate the desired type of tissue according to known scientific values.

As can be seen from the mathematics involved in the equation, r can be up to four separate values for each given value for theta.

Example 1

If V=2495 Volts; a=0.7 cm; and A=650 V/cm;
Then $b^2=1.376377$
and then a cassini curve can be plotted by using eq. (5) above by solving for r, for each degree of theta from 0 degrees to 360 degrees.

A portion of the solutions for eq. (5) are shown in Table 1 below:
where $M=a^2 \cos(2*\text{theta})$; and $L=\text{sqrt}(b^4-a^4 \sin^2(2*\text{theta}))$

TABLE 1

| Theta (degrees) | r = sqrt(M + L) | r = -sqrt(M + L) | r = sqrt(M - L) | r = -sqrt(M - L) |
|---|---|---|---|---|
| 0 | 1.366154 | -1.36615 | 0 | 0 |
| 1 | 1.366006 | -1.36601 | 0 | 0 |
| 2 | 1.365562 | -1.36556 | 0 | 0 |
| 3 | 1.364822 | -1.36482 | 0 | 0 |
| 4 | 1.363788 | -1.36379 | 0 | 0 |
| 5 | 1.362461 | -1.36246 | 0 | 0 |
| 6 | 1.360843 | -1.36084 | 0 | 0 |
| 7 | 1.358936 | -1.35894 | 0 | 0 |
| 8 | 1.356743 | -1.35674 | 0 | 0 |
| 9 | 1.354267 | -1.35427 | 0 | 0 |
| 10 | 1.351512 | -1.35151 | 0 | 0 |
| 11 | 1.348481 | -1.34848 | 0 | 0 |
| 12 | 1.34518 | -1.34518 | 0 | 0 |
| 13 | 1.341611 | -1.34161 | 0 | 0 |
| 14 | 1.337782 | -1.33778 | 0 | 0 |
| 15 | 1.333697 | -1.3337 | 0 | 0 |

The above eq. (6) was developed according to the following analysis.

The curve from the cassini oval equation was calibrated as best as possible to the 650 V/cm contour line using two 1-mm diameter electrodes with an electrode spacing between 0.5-5 cm and an arbitrary applied voltage.

For this worksheet, $q_1$ and $q_2$ reference points (taken to be +/- electrodes) could be moved to locations along the x-axis to points of (±a,0). A voltage could then be selected, and an arbitrary scaling factor ("gain denominator") would convert this voltage to the corresponding "b" used in eq. (4). The worksheet would then plot the resulting Cassini oval, which has a shape progression with applied voltage beginning as two circles around the electrodes that grow into irregular ellipses before converging into a single "peanut" shape that ultimately becomes an ellipse expanding from the original electrode locations.

The Cassini oval creates a reasonable visualization that mimics the shape of numerical results for the field distribution. In order to understand which values or levels correspond to a desired electric field of interest, a calibration involving the $b^4$ term was necessary to develop the relationship between the analytical Cassini oval and the numerical results. This was done through a backwards calibration process defined as follows:

1. A reference contour was selected to correlate the analytical and numerical solutions. This was chosen to be when b/a=1, forming a lemniscate of Bernoulli (the point where the two ellipses first connect, forming "∞").

2. A reference electric field density value was selected to be 650 V/cm.

3. Numerical models were developed to mimic the x-y output from the Cassini oval for scenarios where a=±0.25, 0.5, 0.75, 1.0, 1.25, 1.5, 1.75, 2.0, 2.25, and 2.5 cm.

4. Models were solved using trial and error to determine which voltage yielded the electric field contour of 650 V/cm In the shape of a lemniscate of Bernoulli.

5. The determined voltage was placed into the Cassini oval electronic worksheet for the same electrode geometry and the "gain denominator" was adjusted until the shape from the cassini oval matched that from the numerical solution.

6. The determined gain denominators for all values of "a" were collected and a calibration plot was made and fitted with a logarithmic trendline of:

$$\text{Gain Denominator}=595.28 \cdot \ln(a)+2339;\ R^2=0.993 \quad (7)$$

7. The calibration trendline function shown above was incorporated back into the Cassini Oval spreadsheet. At this point, the worksheet was capable of outputting a field contour of 650 V/cm for any electrode separation distance (±a) and applied voltage (V).

8. The calibration function was then scaled to a desired electric field contour input. This allowed the analytical solution to solve for any electric field for any given a separation distance and voltage. Since the Laplace equation is linear, scaling should provide a good estimate for how other fields would look.

Table 1 incorporates all the steps above to yield a single, calibrated Cassini Oval output that analytically predicts the electric field distribution; providing a quick and simple solution for the prediction of IRE (irreversible electroporation) treatment regions that may be adjusted in real-time. The inputs are the electrode location (as a given "±a" distance from the origin along the x-axis), the applied voltage to the energized electrode, and the desired electric field to visualize. The resulting output is a contour representing a threshold where the entire area within it has been subjected to an electric field≥the one selected; and thus treated by IRE. It is important to remember that the analytical solution was calibrated for an electric field contour of 650 V/cm, and thus yields an accurate approximation for this value. Other field strength contours of interest still yield reasonable results that mimic the overall shape of the electric field. Overall, the analytical solution provided yields consistently good predictions for electric field strengths, and thus, treatment regions of IRE that may be used during treatment planning or analysis.

A similar algorithm for calibration can be used for a bipolar electrode.

In one example, the diameter of the probe is 0.065 cm, and the lengths of the two electrodes are respectively 0.295 cm and 0.276 cm, separated by an insulation sleeve of 0.315 cm in length. Adapting this scenario to the cassini oval presents some challenges because the distribution is now resulting from the two exposed cylinder lengths, rather than two distinct loci of points. This was solved by calibrating individual electric field contours for the same applied voltage and developing two equations that adjust the separation distance (±a) and gain denominator (GD) according to the equations:

$$a = 7*10^{-9}*E^3 - 2*10^{-5}*E^2 + 0.015*E + 6.1619;$$
$$R^2 = 0.9806 \qquad (8)$$

$$GD = 1.0121*E + 1920; \quad R^2 = 0.9928 \qquad (9)$$

where E is the electric field magnitude contour desired. These two equations may then be used to calibrate the cassini ovals into a satisfactory shape to mimic the electric field distribution, and thus treatment region accordingly.

FIG. 6 illustrates an example of how to generate a combined treatment zone according to the invention. Three electrodes 201, 202, 203 defining three individual treatment zones 311, 312, 313, combine to form a combined treatment region 315 which is shown with hatched lines. By combining a plurality of treatment zones with each treatment zone being defined by a pair of electrodes, a combined treatment region 315 can be displayed on the x-y grid.

Figure 7:
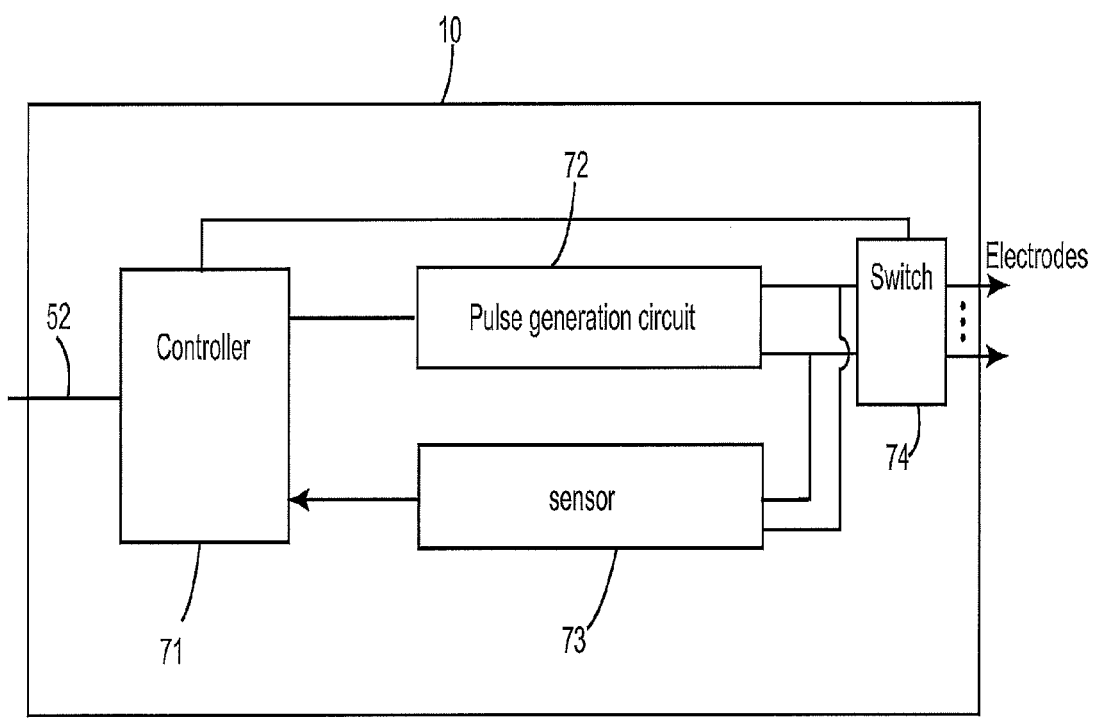
FIG. 7 illustrates details of the generator shown in FIG. 1.

FIG. 7 illustrates one embodiment of a pulse generator according to the present invention. A USB connection 52 carries instructions from the user computer 40 to a controller 71. The controller can be a computer similar to the computer 40 as shown in FIG. 2. The controller 71 can include a processor, ASIC (application-specific integrated circuit), microcontroller or wired logic. The controller 71 then sends the Instructions to a pulse generation circuit 72. The pulse generation circuit 72 generates the pulses and sends electrical energy to the probes. In the embodiment shown, the pulses are applied one pair of electrodes at a time, and then switched to another pair using a switch 74, which is under the control of the controller 71. The switch 74 is preferably an electronic switch that switches the probe pairs based on the instructions received from the computer 40. A sensor 73 such as a sensor can sense the current or voltage between each pair of the probes in real time and communicate such information to the controller 71, which in turn, communicates the information to the computer 40. If the sensor 73 detects an abnormal condition during treatment such as a high current or low current condition, then it will communicate with the controller 71 and the computer 40 which may cause the controller to send a signal to the pulse generation circuit 72 to discontinue the pulses for that particular pair of probes.

The treatment control module 54 can further include a feature that tracks the treatment progress and provides the user with an option to automatically retreat for low or missing pulses, or over-current pulses (see discussion below). Also, if the generator stops prematurely for any reason, the treatment control module 54 can restart at the same point where it terminated, and administer the missing treatment pulses as part of the same treatment.

In other embodiments, the treatment control module 54 is able to detect certain errors during treatment, which include, but are not limited to, "charge failure", "hardware failure", "high current failure", and "low current failure".

Figure 8:
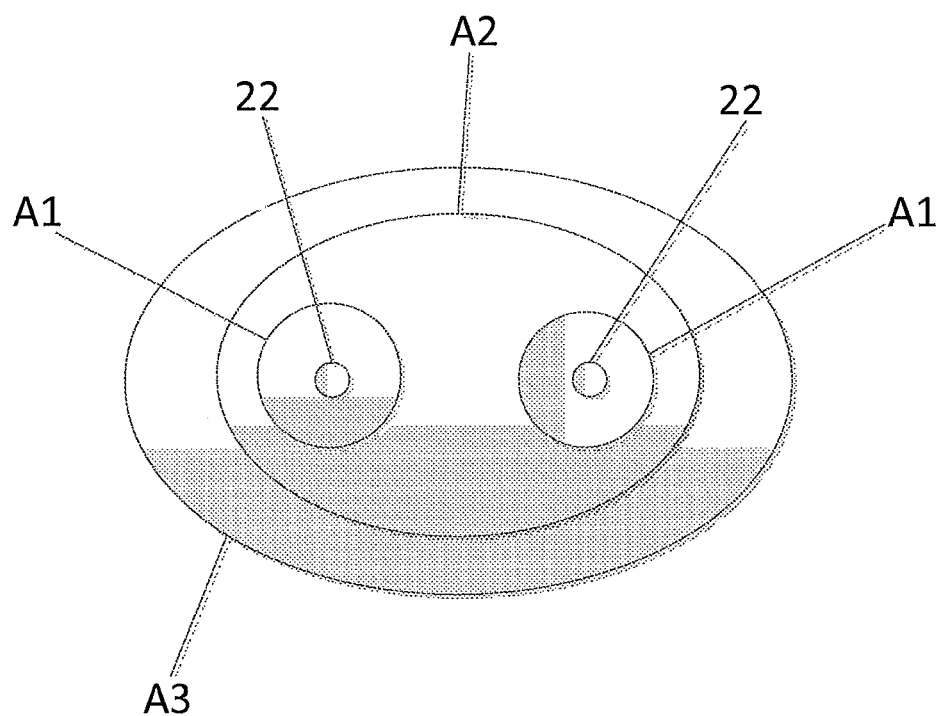
FIG. 8 illustrates an image of a sample pre-conditioned tissue zone surrounded by a sample ablation zone.

According to the invention, the treatment control module 54 in the computer 40 directs the pulse generator 10 to apply a plurality of ore-conditioning pulses (first set of pulses) between the electrodes 22 so as to create "virtual electrode" (i.e., pre-conditioning zone) A1 as shown in FIG. 8. Once the pre-conditioning zone has been created, the control module 54 directs the generator to apply a plurality of treatment pulses (second set of pulses) to the electrodes 22 to ablate substantially all tissue cells in the target ablation zone.

If the treatment pulses were applied without the pre-conditioning pulses, then the expected target ablation zone would result in zone A2. However, due to the pre-conditioning zone A1, the resulting ablation zone has been enlarged to zone A3 which is much larger than zone A2.

As shown in FIG. 8, the pre-conditioned tissue zone A1 is substantially surrounded by ablation zones A2 and A3. In one exemplary embodiment, at least two electrodes 22 can be provided. The electrodes can be positioned anywhere in or near the target tissue.

The pre-conditioning pulses can be 1) IRE pulses that irreversibly electroporate the cell membranes in zone A1, 2) reversible electroporation pulses that temporarily electroporate the cell membranes in zone A1, or 3) pulses that cause irreversible electroporation to some cells and reversible electroporation in other cells in the zone. Alternatively, the pre-conditioning pulses can even be supraporation type pulses (typically sub-microsecond pulses, with 10-80 kV/cm of field strength) that causes disturbances within the cells which tend to weaken them such that when the treatment pulses are applied, the cells in zone A1 are more vulnerable to irreversible electroporation even when the voltage applied may be sufficient for only reversible electroporation. The particular pre-conditioning pulse parameters would depend on many factors such as the type of tissue and the size of zone A1 to be created.

The mechanism of action for the increased conductivity in the virtual electrode as follows. There is a range of non thermal irreversible electroporation (NTIRE). At one end of the range, there is just enough irreversible cell membrane age to cause cell death. At the other end of the range, there is so much cell membrane damage that the membrane ruptures (similar to a balloon popping). The virtual electrode (highest conductivity tissue) works well in the tissue where the cell membranes have ruptured. Accordingly, the pre-conditioning pulses are preferably those that are capable of causing NTIRE which also causes cell rupturing to at least some of the tissue cells in the pre-conditioning zone. In another aspect, the pre-conditioning pulses are capable of causing NTIRE which also causes cell rupturing to substantially all tissue cells in the pre-conditioning zone.

After the target tissue is pre-conditioned using pre-conditioning electrical pulses, the control module 54 directs the pulse generator 10 to apply a set of treatment pulses, thereby forming a second zone of ablation A3 that substantially surrounds pre-conditioning zone A1. As noted above, zone A3 is substantially larger than zone A2 which would be the result from application of only the treatment pulses without the pre-conditioning pulses.

To pre-condition at least a portion of the target tissue, a first set electrical pulses can be delivered to the cells of the target tissue A1 at a predetermined voltage to form a pre-conditioned zone. In one aspect, the applied current tip delivered or electrical impedance during the pre-conditioning pulse application can be measured to adjust the pulse parameters such as the number of pulses that need to be delivered to create the pre-conditioned tissue zone A1. Optionally, one or more test pulses can be delivered to the electrodes before delivering the first set of electrical pulses. In one aspect, the applied current/impedance can be measured using the sensor 73 during the delivery of the test pulses, and any pulse parameter such as the voltage, number of pulses, and the duration of the pulses can be adjusted to create the desired pre-conditioned tissue zone A1 based on the measured current or impedance. In one exemplary embodiment, the first and second sets of electrical pulses can be delivered to the target tissue in the range of from about 2,000 V/cm to about 3,000 V/cm.

After the target tissue is pre-conditioned using a first set of electrical pulses, optionally, a predetermined time delay can be commenced before delivering a second set of electrical pulses to the target tissue to allow intra-cellular fluid to escape thereby further increasing the conductance of zone A1. In one exemplary embodiment, the predetermined time delay between the first set of electrical pulses and the second set of electrical pulses can be from about 1 second to about 10 minutes to allow for mixing of intra-cellular and extra-cellular components. Preferably, the waiting period ranges from 30 seconds to 8 minutes, and more preferably 2 minutes to 8 minutes, to allow sufficient time for the intra-cellular fluid to exit the cells.

Alternatively, the treatment control module applies a test pulse through the electrode after the pre-conditioning pulses have been applied. Based on the applied test pulse, the module 54 determines whether to repeat the application of the pre-conditioning pulses or proceed to application of the treatment pulses. In one aspect, the treatment control module 54 determines whether to repeat the application of the pre-conditioning pulses based on an electrical conductivity derived from the test pulse. For example, if the electrical conductivity has not been sufficiently increased, the module may decide to repeat the application of pre-conditioning pulses with perhaps lower voltage or shorter pulse width than before.

Modeling for the increased ablation area due to an increase in electrode size is known in the adz. See, for example, an article by Edd entitled "Mathematical Modeling of Irreversible Electroporation for Treatment Planning", published in Technology in Cancer Research and Treatment, August 2007, Vol. 6, No. 4, pages 275-286, which is incorporated herein by reference. For more accuracy, experiments could be performed to modify the equations discussed herein.

In one aspect, the first set of electrical pulses can comprise about 10 pulses to about 100 pulses. More preferably, the first set of electrical pulses can comprise from about 10 pulses to about 50 pulses. Still more preferably, the first set of electrical pulses can comprise from about 10 pulses to about 20 pulses. In one exemplary embodiment, the first set of electrical pulses can be delivered to the target tissue with each pulse having a pulse duration in a range of from about 10 μsec to about 50 μsec at a voltage between the two electrodes of 2000 to 3000 Volts. In another embodiment, the pre-conditioning electrical pulses can be delivered to the target tissue with each pulse having a duration in a range of from about 10 μsec to about 20 μsec. It has been observed that large ablations using irreversible electroporation require longer pulse widths or durations than smaller pulse width ablations. Narrower pulse widths such as those described herein may be beneficial because such pulses will substantially affect the tissue close to the electrodes 22, with a reduced risk of over-current conditions and reduced joule heating. For example, applying pulses of 20 μsec width will cause irreversible electroporation of a narrow band of tissue substantially around the electrodes 22. The delivery of the first set of electrical pulses can be repeated until a predetermined level of conductivity/impedance is measured in the target tissue. Alternatively, the delivery of the first set of electrical pulses can be repeated until a predetermined number of electrical pulses is delivered to the target tissue. In one example, the predetermined number of pulses can be between about 10 pulses and about 300 pulses. In another example, the predetermined number of pulses can be about 100 pulses.

Pre-conditioning the tissue zone A1 around the electrodes 22 causes the tissue surrounding the electrodes 22 to be more conductive and increases the ability of the tissue to electrically couple to the electrodes. If the electrical coupling between the electrodes and the target tissue is enhanced, this allows higher voltages to be delivered and larger ablations to be created. The higher conductivity of the tissue also helps to increase the ablation size of the tissue and to reduce the incidence of arcing from the electrode tips. As the target tissue is pre-conditioned by being irreversibly electroporated, an electric field gradient is established where the target tissue is most conductive near the electrodes 22. In one aspect, the pre-conditioned tissue allows the electric; field gradient to become steeper compared to non-pre-conditioned target tissue.

The second set of electrical pulses (treatment pulses) can comprise at least 10 pulses and in one embodiment, about 10 pulses to about 100 pulses. In another embodiment, the second set of electrical pulses can comprise about 10 pulses to about 50 pulses. In yet another embodiment, the second set of electrical pulses can comprise about 10 pulses to about 20 pulses. In one exemplary embodiment, the second set of electrical pulses can be delivered to the target tissue with each pulse having a duration in a range of from about 70 μsec to about 100 μsec at a voltage between the two electrodes of 2000 to 3000 Volts. Alternatively, the second set of pulses (treatment pulses) may be supra-poration pulses that have a pulse with of 1 microsecond or less and a voltage of 10 kV/cm or more. Still in another alternative embodiment, the second set of electrical pulses have a pulse width of 0.3 microsecond to 10 microseconds and a pulse application frequency of 50 kHz or higher. The higher frequency of the pulses may reduce or even eliminate movement of the patient and may allow treatment of a zone made of different tissue types.

The delivery of an additional second set of pulses to the target tissue and/or the use of predetermined time delays between sets of pulses helps to further increase the ablation zone of the irreversibly electroporated tissue to electric field thresholds that are lower than currently published values. In one embodiment, the first predetermined voltage of the first set of electrical pulses can be greater than the second predetermined voltage of the second set of electrical pulses. In another embodiment, the first predetermined voltage of the first set of electrical pulses can be less than the second predetermined voltage. In yet another embodiment, the first predetermined voltage can be substantially equal to the second predetermined voltage. Typically, however, compared to the pre-conditioning pulses, the treatment pulses have a higher pulse width, higher voltage or both.

In one aspect, the virtual electrode A1 can comprise target tissue that has been severely electroporated. Severe electroporation is the formation of pores in cell membranes by the action of high-voltage electric fields. When the cells of the target tissue are severely electroporated, the intracellular components of the cells of the target tissue are destroyed in a very short amount of time, i.e., several minutes compared to two hours to one day in irreversibly electroporated target tissue. The severe electroporation of the cells of the target tissue results in a fatal disruption of the normal controlled flow of material across a membrane of the cells in the target tissue, such that the target tissue comprises substantially no intracellular components. When severely electroporated, the cells of the target tissue catastrophically fail, yet the target tissue cell nuclei are still intact. When severe electroporation occurs and sufficient intra-cellular components have been excreted from the cells of the target tissue, this helps to make cells of the target tissue locally and highly conductive. When the tissue around the electrodes is highly porated, the local tissue resistance is greatly reduced, and the tissue will couple better to the active electrode. The severely electroporated tissue thus forms a virtual electrode to all a substantial increase in the target ablation zone.

Figure 9:
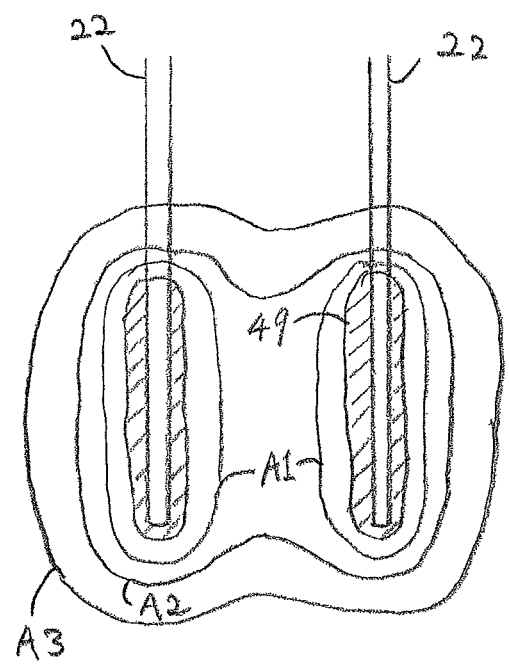
FIG. 9 illustrates another image of a sample pre-conditioned tissue zone surrounded by a sample ablation zone.

FIG. 9 illustrates at least two severe electroporation zones 49 that are positioned such that they substantially surround at least a portion of the electrodes 22. In these areas of severe electroporation the electrical fields are very high. These areas of target tissue having increased electrical field strength can also have local edema, which is an abnormal accumulation of fluid beneath the skin or in one or more cavities of the body that produces swelling. The increased local fluid content in the target tissue will improve electrical coupling of the target tissue to the electrodes 22. The higher local fluid content will help keep the outer surface of the electrode wet. Further, the mixing of intra-cellular contents that have a high ionic content with extracellular fluid contents that have a lower ionic content can increase the local conductivity of the target tissue.

In yet another aspect, an agent can be provided and delivered to the target tissue before, during, or after an ablation to improve electrical coupling between the electrode and the target tissue. The agent can be a surface tension modifier, a wetting agent, a liquid, a gel, or any combination thereof. The agent can be delivered through the electrodes to the target tissue, in one exemplary embodiment, one or more of the electrodes 22 can have openings positioned along the outer surface of the electrodes 22. The openings of the electrodes 22 can be in fluid communication with an inner lumen of the electrodes. An agent can be delivered through the lumen of one or more of the electrodes 22 along the outer surface of the electrodes 22. In one exemplary embodiment, the one or more agents can be diffused along the entire length of the electrodes 22 before, during, or after a target tissue ablation. Additional benefits "wetting" the target tissue either through the target tissue's increased fluid content, as described above, or by manually providing a wetting agent, include a reduced probability of arcing from the electrode to the target tissue. A larger ablation area can also be created by using a larger virtual electrode, as illustrated in FIG. 8. Further, reduced Joule heating occurs around the electrodes 22 as a result of the delivery of shorter or narrower width pulses or pulse durations to the target tissue, which also requires less applied energy. In yet another aspect, a high conductivity fluid can be infused into the target tissue before, during, or after the ablation to increase the local conductivity of the target tissue near the electrodes 22. In one exemplary aspect, the high conductivity fluid can be, e.g., hypertonic saline or a similar liquid.

In one embodiment, the ablation process as described above, including the progress thereof, can be monitored by detecting the associated change in impedance (either real, imaginary or complex) through the sensor 73 in the ablated tissue for both the pre-conditioning step and treatment pulse application step. In the pre-conditioning step, once the outer perimeter of the ablated, liquid-like pre-conditioned tissue is defined, the impedance can stabilize or level out. Thus, the progress of the preconditioning step can be monitored by measuring changes in impedance, and pre-conditioning pulse application can be discontinued once a change in impedance is no longer observed. Alternatively, once the pre-conditioning pulses have been applied, the treatment control module 54 continuously monitors the change in impedance of tissue between the two electrodes. The impedance should decrease as conductive intra-cellular fluid from the pre-conditioned tissue cells starts to ooze out. Once a predetermined impedance (or a predetermined impedance decrease) has been reached, the treatment control module 54 moves to the step of applying the treatment pulses between the electrodes.

In another embodiment, the applied current of the electrical pulses can be continuously measured during pre-conditioning pulse application, and the number of pulses, the voltage level, and the length of the pulses can be adjusted to create a predetermined virtual electrode.

Although the present treatment method has been discussed in relation to irreversible electroporation (IRE), the principles of this invention can be applied to any other method where therapeutic energy is applied at more than one point. For example, other methods can include reversible electroporation, supraporation, RF ablation, cryo-ablation, microwave ablation, etc. "Supraporation" uses much higher voltages, in comparison to electroporation, but with shorter pulse widths.

In addition to the example parameters described above, specific electro-medical applications of this technology include reversible electroporation as well as irreversible electroporation. This could include reversible or irreversible damage to the external cell membranes or membranes of the organelles, or damage to individual cellular structures such as mitochondrion so as to affect cellular metabolism or homeostasis of voltage or ion levels. Example embodiments for reversible electroporation can involve 1-8 pulses with a field strength of 1-100 V/cm. Other embodiment altering cellular structure adversely involve supraporation pulse generators having a voltage range of 100 kV-300 kV operating with nano-second (sub-microsecond) pulses with a minimum field strength of 2,000 V/cm to and in excess of 20,000 V/cm between electrodes. Certain embodiments involve between 1-15 pulses between 5 microseconds and 62,000 milliseconds, while others involve pulses of 75 microseconds to 20,000 milliseconds. In certain embodiments the electric field density for the treatment is from 100 Volts per centimeter (V/cm) to 7,000 V/cm, while in other embodiments the density is 200 to 2000 V/cm as well as from 300 V/cm to 1000 V/cm. Yet additional embodiments have a maximum field strength density between electrodes of 250 V/cm to 500 V/cm. The number of pulses can vary. In certain embodiments the number of pulses is from 1 to 100 pulses. In one embodiment, as described herein, between about 10 pulses and about 100 pulses can be applied at about 2,000 V/cm to about 3,000 V/cm with a pulse width of about 10 μsec to about 50 μsec. After applying these pulses, a pre-determined time delay of from about 1 second to about 10 minutes can optionally be commenced in order that intra-cellular contents and extra-cellular contents of the target tissue cells can mix. This procedure can be repeated, as necessary, until a conductivity change is measured in the tissue. Following this step, about 1 pulse to about 300 pulses of about 2,000 V/cm to about 3,000 V/cm can be applied with a pulse width of about 70 μsec to about 100 μsec to widely ablate the tissue. This last step can be repeated until a desired number of ablation pulses is delivered to the tissue, for example, in the range of about 10 pulses to about 300 pulses, more particularly, about 100 pulses. In other embodiments, groups of 1 to 100 pulses (here groups of pulses are also called pulse-trains) are applied in succession following a gap of time. In certain embodiments the gap of time between groups of pulses is 0.5 second to 10 seconds.

In summary, a method of increasing the ablation size in a living mammal such as a human is executed by the system, which includes the computer 40 storing the treatment control module 54 and the generator 10. The treatment control module executes the following steps. The size, shape, and position of a lesion are identified with an imaging device 30. The treatment control module 54 as described above is started by a user. The dimensions of the lesion, the type of probe device, and other parameters for treatment are received either automatically or through user inputs. Based on these inputs, the treatment control module 54 generates a lesion image placed on a grid. Based on the lesion size and the number of probes/electrodes to be used, the treatment module determines whether it is sufficiently large to require pre-conditioning steps according to the present invention. If so, the control module 54 automatically sets the probe locations and generates an estimated target zone superimposed on the lesion image based on the enlarged ablation target zone expected from adding the pre-conditioning step.

The user is allowed to click and drag each of the probes/electrodes. The user can verify that the image of the lesion is adequately covered by the ablation region that is estimated by the treatment control module 54. If necessary, the user can select a treatment device with additional probes or make other adjustments. The user can then physically place the probes in the patient based on the placement which was selected on the grid. The user can adjust the placement of the probes on the grid if necessary based on the actual placement in the patient. The user is now ready to treat the tissue as described above.

Therapeutic energy deliver devices disclosed herein are designed for tissue destruction in general, such as resection, excision, coagulation, disruption, denaturation, and ablation, and are applicable in a variety of surgical procedures, including but not limited to open surgeries, minimally invasive surgeries (e.g., laparoscopic surgeries, endoscopic surgeries, surgeries through natural body orifices), thermal ablation surgeries, non-thermal surgeries, as well as other procedures known to one of ordinary skill in the art. The devices may be designed as disposables or for repeated uses.

The above disclosure is intended to be illustrative and not exhaustive. This description will suggest many modifications, variations, and alternatives may be made by ordinary skill in this art without departing from the scope of the invention. Those familiar with the art may recognize other equivalents to the specific embodiments described herein. Accordingly, the scope of the invention is not limited to the foregoing specification.

The invention claimed is:

1. A method comprising the steps of:
positioning at least one electrode near a target ablation zone;
applying through the at least one positioned electrode a plurality of pre-conditioning pulses, wherein the pre-conditioning pulses are irreversible electroporation pulses and result in a pre-conditioning zone surrounding the at least one positioned electrode, the pre-conditioning zone being smaller than the target ablation zone;
monitoring a current of the plurality of pre-conditioning pulses using a treatment control module; and
applying through the at least one positioned electrode a plurality of treatment pulses capable of irreversibly electroporating cells within the target ablation zone.

2. The method of claim 1, wherein the step of applying the plurality of treatment pulses further comprises applying the plurality of treatment pulses in an amount sufficient to subject the target ablation zone to supra-poration.

3. The method of claim 1, wherein the step of applying the plurality of pre-conditioning pulses further comprises applying pre-conditioning pulses that have a shorter pulse width than the treatment pulses.

4. The method of claim 1, further comprising the step of waiting at least 30 seconds to allow an electrical conductivity in the pre-conditioning zone to increase.

5. The method of claim 1, further comprising the step of waiting at least two minutes to allow an electrical conductivity in the pre-conditioning zone to increase.

6. The method of claim 1, further comprising the steps of:
applying a test pulse through the at least one electrode after the pre-conditioning pulses have been applied; and
determining whether to repeat the application of the pre-conditioning pulses or proceed to application of the treatment pulses based on of a measured electrical conductivity.

7. A method comprising:
positioning at least one electrode near a target ablation zone;
applying through the at least one positioned electrode a plurality of pre-conditioning pulses, Wherein the pre-conditioning pulses are irreversible electroporation pulses and result in a pro-conditioning zone surrounding the at least one positioned electrode, the pre-conditioning zone being smaller than the target ablation zone;
monitoring for a change in an impedance of the plurality of pre-conditioning pulses using a treatment control module;
adjusting at least one pulse parameter of the plurality of pre-conditioning pulses if a change in the impedance of the plurality of pre-conditioning pulses is observed; and
applying through the at least one positioned electrode a plurality of treatment pulses capable of irreversibly electroporating cells within the target ablation zone after the pre-determined impedance threshold has been met.

8. The method of claim 7, wherein the pre-conditioning pulses and treatment pulses are delivered by a generator.

9. The method of claim 7, wherein the at least one pulse parameter of the plurality of pre-conditioning pulses comprises the voltage.

10. The method of claim 7, wherein the at least one pulse parameter of the plurality of pre-conditioning pulses comprises the number of pulses.

11. The method of claim 7, wherein the at least one pulse parameter of the plurality of pre-conditioning pulses comprises the duration of the pulses.

12. A method comprising the steps of:
positioning at least two electrodes near a target ablation zone;
applying through the positioned electrodes at least two pre-conditioning pulses, wherein the pre-conditioning pulses are irreversible electroporation pulses and result in a pre-conditioning zone, wherein the pre-conditioning zone is smaller than the target ablation zone;
monitoring a treatment parameter of the pre-conditioning pulses using a treatment control module; and
applying through the positioned electrodes a plurality of treatment pulses capable of irreversibly electroporating cells within the target ablation zone.

13. The method of claim 12, wherein the step of monitoring is done in real time.

14. The method of claim 12, wherein the treatment parameter comprises a change in current or a change in impedance.

15. The method of claim 14, wherein the treatment control module continuously monitors the treatment parameter after the pre-conditioning pulses have been applied.

16. The method of claim 12, further comprising the step of:
   displaying the monitored treatment parameter of the pre-conditioning pulses on a display unit.

17. The method of claim 12, wherein applying the pre-conditioning pulses results in an increase in conductivity to the pre-conditioning zone.

18. The method of claim 12, wherein the pre-conditioning pulses and treatment pulses are delivered by a generator.

19. The method of claim 15, further comprising the step of:
   adjusting a pulse parameter in response to the monitored treatment parameter.

20. The method of claim 19, wherein the pulse parameter comprises voltage of the pre-conditioning pulses, number of the pre-conditioning pulses, or duration of the pre-conditioning pulses.

* * * * *